United States Patent [19]

Sakagami

[11] Patent Number: 5,055,262
[45] Date of Patent: Oct. 8, 1991

[54] AUTOMATIC CUVETTE LOADING APPARATUS

[75] Inventor: Toshio Sakagami, Chofu, Japan

[73] Assignee: Olympus Optical Co., Ltd., Tokyo, Japan

[21] Appl. No.: 311,042

[22] Filed: Feb. 16, 1989

[30] Foreign Application Priority Data

Feb. 22, 1988 [JP] Japan ............................ 63-21107[U]

[51] Int. Cl.$^5$ ............................................ G01N 21/13
[52] U.S. Cl. ....................................... 422/64; 422/52; 422/65; 436/48
[58] Field of Search ...................... 422/64, 52, 63, 65; 436/48

[56] References Cited

U.S. PATENT DOCUMENTS 4,634,575 1/1987 Kawakami et al. .................. 422/63

FOREIGN PATENT DOCUMENTS 0192957 9/1986 European Pat. Off. .

Primary Examiner—David L. Lacey
Assistant Examiner—Abanti B. Singla
Attorney, Agent, or Firm—Parkhurst, Wendel & Rossi

[57] ABSTRACT

An automatic cuvette loading apparatus for use in an automatic chemical analyzer includes a first slider for moving magazines stocked in a container into a cuvette loading position and for pushing the cuvettes contained in the magazine in a direction perpendicular to a discharging direction, a second slider for pushing a cuvette array situated in the cuvette loading position in the cuvette discharging direction so as to supply the cuvettes to the reaction line one by one, and a third slider for supporting cuvettes in the magazine when the cuvettes are fed in the direction perpendicular to the discharging direction and then the third slider is arranged to be removed from the cuvettes when the cuvettes are loaded into a reaction line of the chemical analyzer. Thus, the cuvettes in the magazine can be loaded without being strongly affected by a frictional force between side walls of the cuvettes and the inner wall of the magazine.

15 Claims, 7 Drawing Sheets

FIG_3

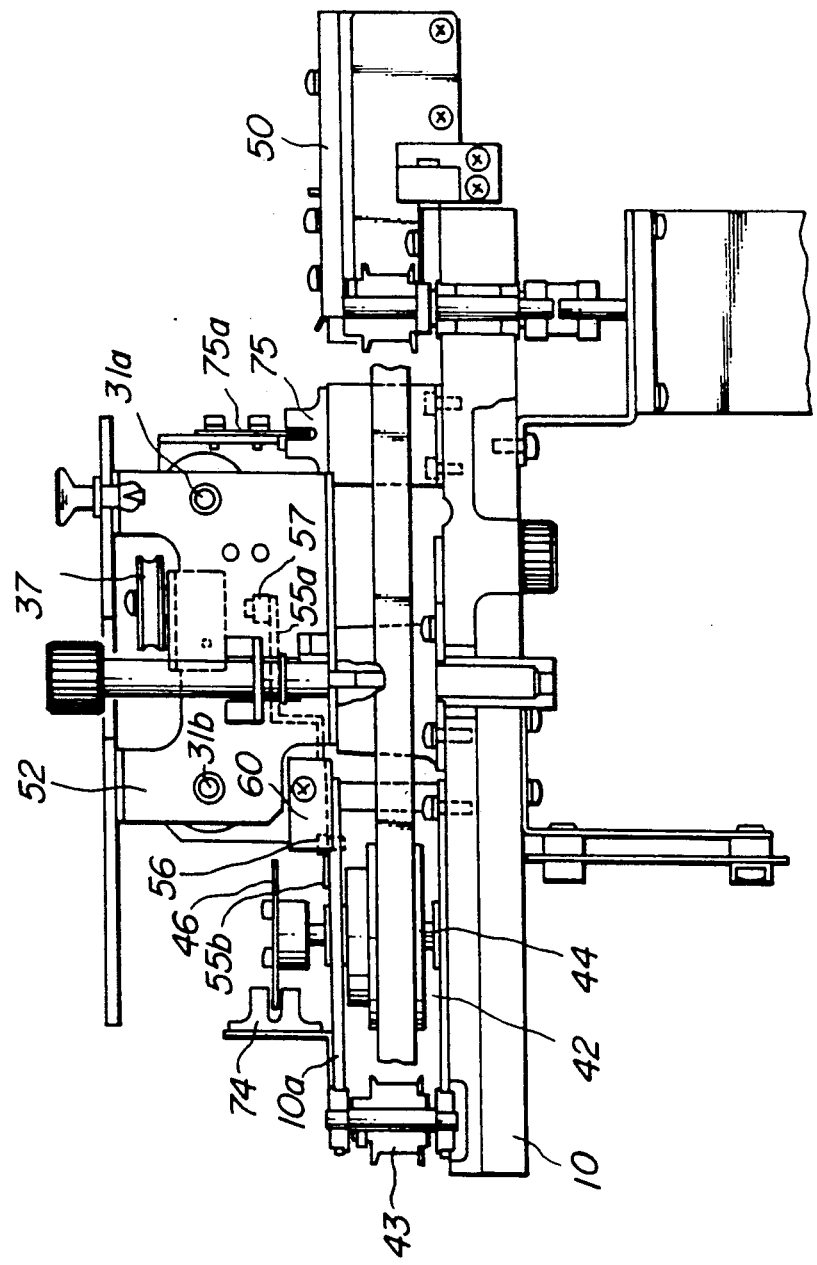

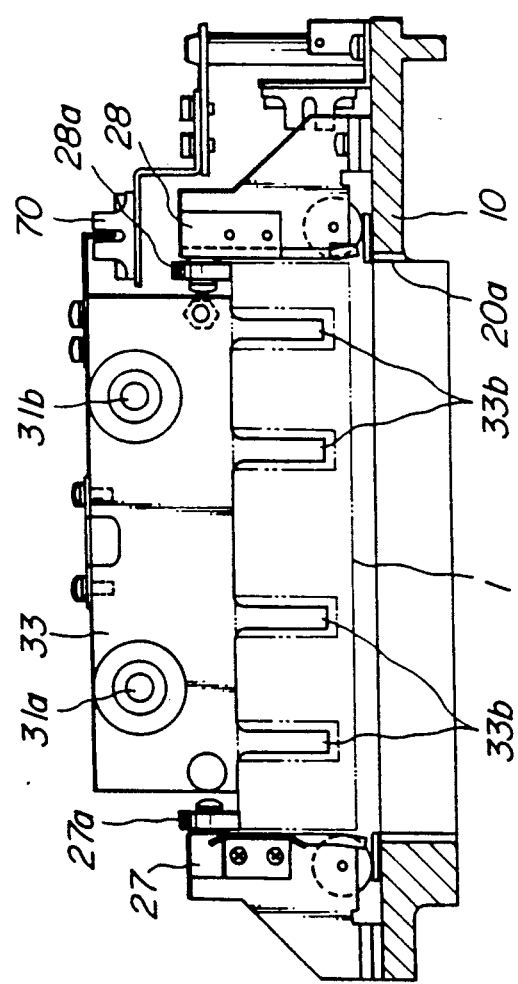
FIG_7

AUTOMATIC CUVETTE LOADING APPARATUS

BACKGROUND OF THE INVENTION

Field of the Invention and Related Art Statement

The present invention relates generally to chemical analysis, and more particularly to a cuvette auto-loading apparatus for successively supplying cuvettes into a reaction line of an automatic chemical analyzer.

There have been proposed various types of automatic chemical analyzers. In a calorimetric analyzer, a sample such as a serum and a reagent are delivered into a cuvette fed along a reaction line to form a test liquid and then the light absorption of the test liquid is photometered to effect a quantitative analysis. Such analyzers may be classified into a direct measuring system in which the test liquid contained in the cuvette is photometered and an indirect measuring system in which the test liquid transferred from the cuvette into a flow cell is photometered. From the view point of construction of the analyzer, the former system is superior to the latter system, because the construction can be made much simpler in the former system. As to the treatment of the cuvette, there are two systems. In the first system the cuvettes traveling along the reaction line are used repeatedly, while in the second system used cuvettes are removed from the reaction line and new cuvettes are fed successively into the reaction line. In the first system a mechanism must be provided for washing and drying the cuvettes, so that the whole apparatus is liable to be complicated in construction, large in size and expensive in cost. Further, the first system requires a great amount of a washing liquid and problems occur in treatment of waste washing liquid. If the washing is not effected sufficiently, contamination or carry-over may occur between successive test liquids, which affects the accuracy of measurement. Moreover, while the cuvettes are used repeatedly, they are liable to be damaged or scratched and therefore the measuring accuracy might be decreased. Contrary to this, in the second system the above problem can be entirely removed, because the cuvettes which have been once used are discarded. However, an automatic cuvette loader must be arranged for supplying new cuvettes into the reaction line. Known automatic cuvette loaders have several drawbacks in that they are of complicated construction and require very cumbersome treatment.

In order to solve the above-stated problem, there has been proposed an automatic cuvette loader having a simple construction for certainly supplying cuvettes in the reaction line successively in U.S. Pat. No. 4,634,575. In the automatic cuvette loading apparatus disclosed in U.S. Pat. No. 4,634,575, magazines containing a plurality of cuvettes are stocked in a magazine container of the apparatus and are supplied to the cuvette loading position one by one by means of a first slider which is moved in a first direction. Cuvettes contained in the magazine situated in the cuvette loading position are pushed out of the magazine one by one by sliding a second slider in a second direction perpendicular to the first direction toward the reaction line along a guide shaft to mount the cuvettes in recesses provided in a periphery of a cuvette holder constituting the reaction line of the automatic chemical analyzer. However, when the cuvettes are pushed out of the magazine one by one, it is necessary to align the cuvettes in row in the second direction in order to set the cuvettes in the recesses of the cuvette holder smoothly. In this known cuvette loader, while the side wall of a cuvette row formed by cuvettes situated in the cuvette loading position are urged against the inner wall of the magazine by means of the first slider, the cuvettes are pushed out of the magazine one by one by means of the second slider. Thus, there would occur a frictional force between the side walls of the cuvettes and the inner wall of the magazine, which affects the smooth loading of the cuvettes into the reaction line of the chemical analyzer. A further drawback exists that when the cuvettes are pushed against the inner wall of the magazine by the first slider they might be inclined or when the cuvettes are fed into the reaction line one by one by the second slider, the cuvettes might be caught somewhere in the magazine. Thus, the cuvettes could not be fed into the reaction line smoothly.

SUMMARY OF THE INVENTION

The object of the present invention is to provide a novel and useful automatic cuvette loading apparatus which can feed successive cuvettes into a reaction line of an automatic chemical analyzer in a smooth and stable manner.

According to the invention, an automatic cuvette loading apparatus for use in an automatic chemical analyzer comprises:

a container for containing a plurality of magazines, each containing a plurality of cuvettes in a matrix manner and a plate for feeding a cuvette row, said container having a base plate and first and second openings each having sizes that the magazine can pass therethrough;

means for feeding a magazine situated above the first opening in a first direction into a cuvette loading position above the second opening;

means for supporting the cuvettes in the magazine situated at the cuvette loading position, said cuvette supporting means having a front plate and being movably arranged between a first position at which the front plate is just aligned with a front inner side wall of the magazine with respect to the first direction or slightly inside therefrom and a second position at which the front plate is removed from the front inner side wall of the magazine;

means movably arranged in a second direction perpendicular to the first direction for successively loading the cuvettes contained in the magazine situated at the cuvette loading position into the reaction line of the analyzer one by one; and means for removing an empty magazine from the cuvette loading position through the second opening.

According to the invention, the cuvettes are fed into the reaction line without being affected by a frictional force between the side walls of the cuvettes row situated in the cuvette supplying position and the inner wall of the magazine. Therefore the cuvettes can be moved so smoothly in the cuvette magazine that they are mounted to the cuvette holder of the reaction line one by one without any trouble.

BRIEF DESCRIPTION OF THE DRAWINGS

FIGS. 6 and 7 are right and left side views, respectively illustrating the cuvette loading portion of the embodiment shown in FIG. 4.

DESCRIPTION OF THE PREFERRED EMBODIMENTS

Figure 1:
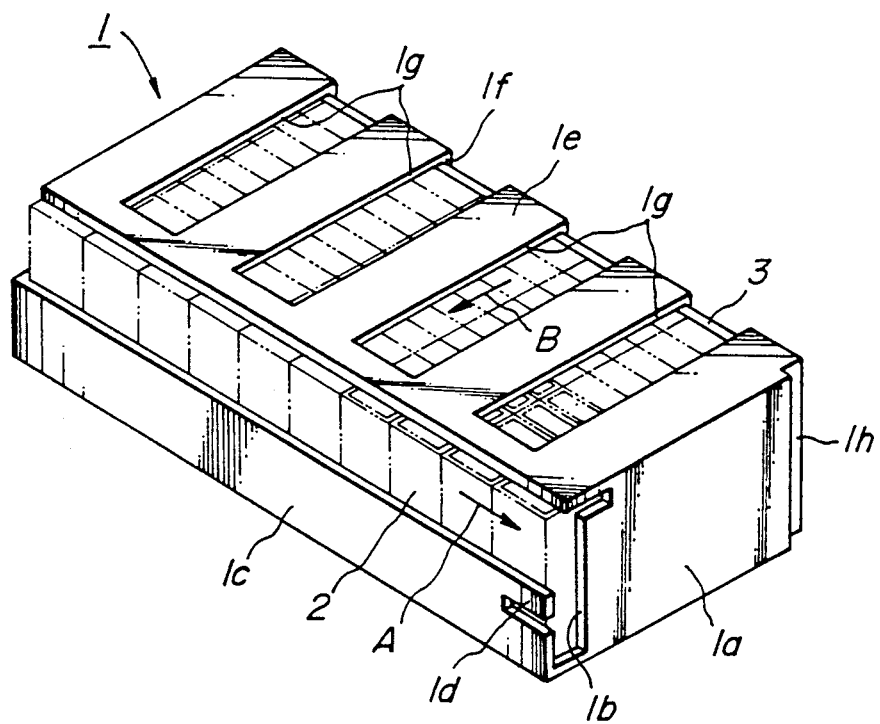
FIG. 1 is a perspective view showing an embodiment of a cuvette magazine containing a plurality of cuvettes in a matrix manner therein to be used in the loading apparatus according to the present invention.

FIG. 1 is a perspective view showing an embodiment of a cuvette magazine for use in the cuvette loader according to the invention. The magazine 1 comprises a rectangular housing formed by a molded plastic or metal. In the present embodiment, the magazine has such a length viewed in a direction A that ten cuvettes are arranged side by side and such a width measured in a direction B that also ten cuvettes are arranged side by side. Therefore, the magazine contains one hundred cuvettes in a matrix form. In a side wall 1a of the magazine 1 is arranged an outlet 1b having a width which is substantially equal to the width of a cuvette 2 and a height which is nearly equal to the height of the cuvette 2. In order to ensure that the cuvette 2 can be discharged out of the magazine 1 through the outlet 1b in a correct posture, a resilient strip 1d is formed in a front wall 1c of the magazine 1 at a position adjacent to the outlet 1b by providing a recess in the wall 1c. As shown in FIG. 1, the front side wall 1c of the magazine has the height which is substantially equal to a half of that of the side wall 1a. In a top wall 1e and a back side wall 1f of the magazine 1 are formed four recesses 1g. It should be noted that the recesses 1g do not extend in the top wall 1e up to the front edge thereof. A push plate 3 is arranged within the magazine 1 between the assembly of cuvettes and the back wall 1f. As will be explained hereinafter, the cuvette array may be moved in the direction B by moving the push plate 3 in this direction B. Along a right hand side edge of the side wall 1a is formed a step 1h which avoids an inverse insertion of the magazine into an automatic cuvette loader having a corresponding projection.

Figure 2:
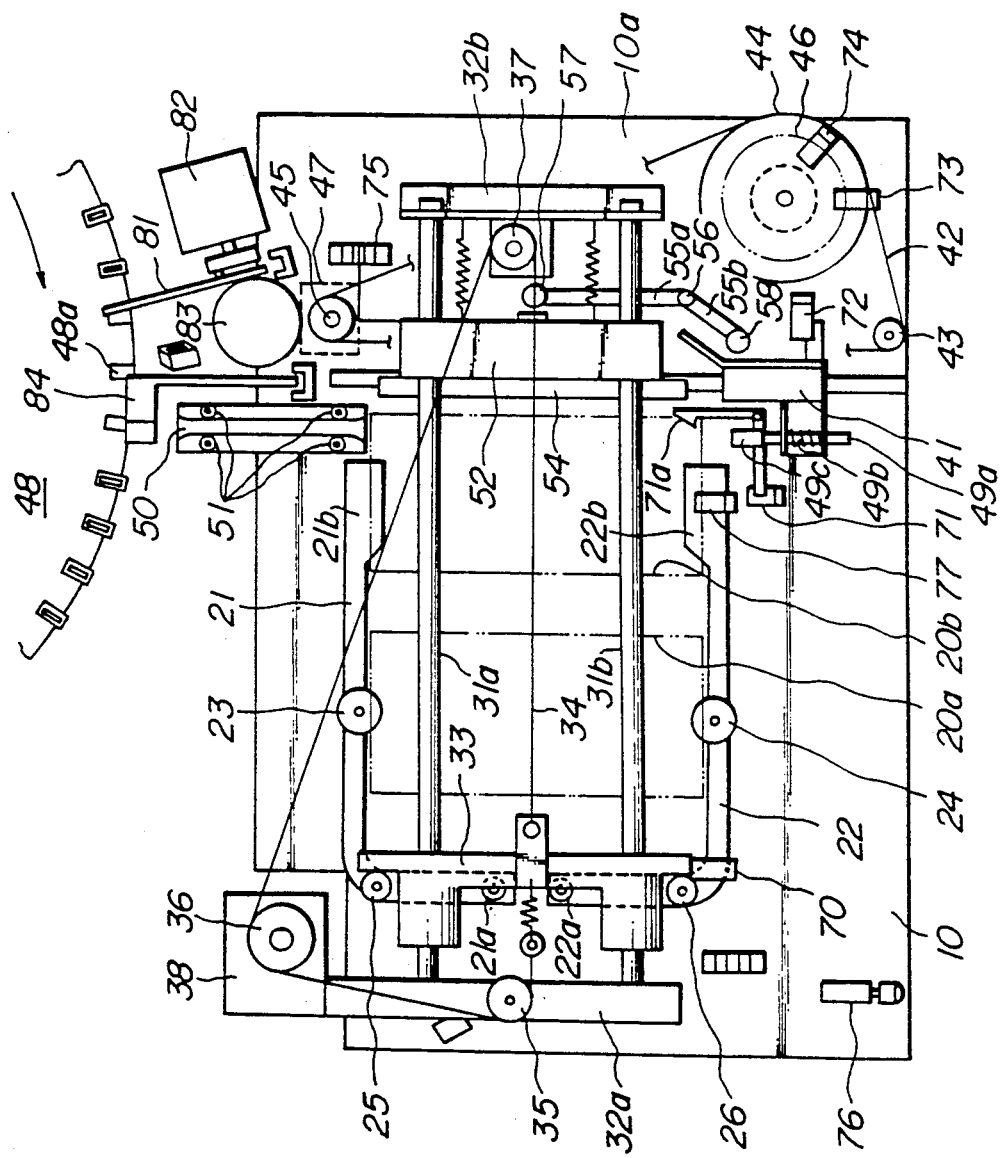
FIG. 2 is a plan view depicting an outline of an embodiment of the automatic cuvette loading apparatus according to the present invention.
Figure 3:
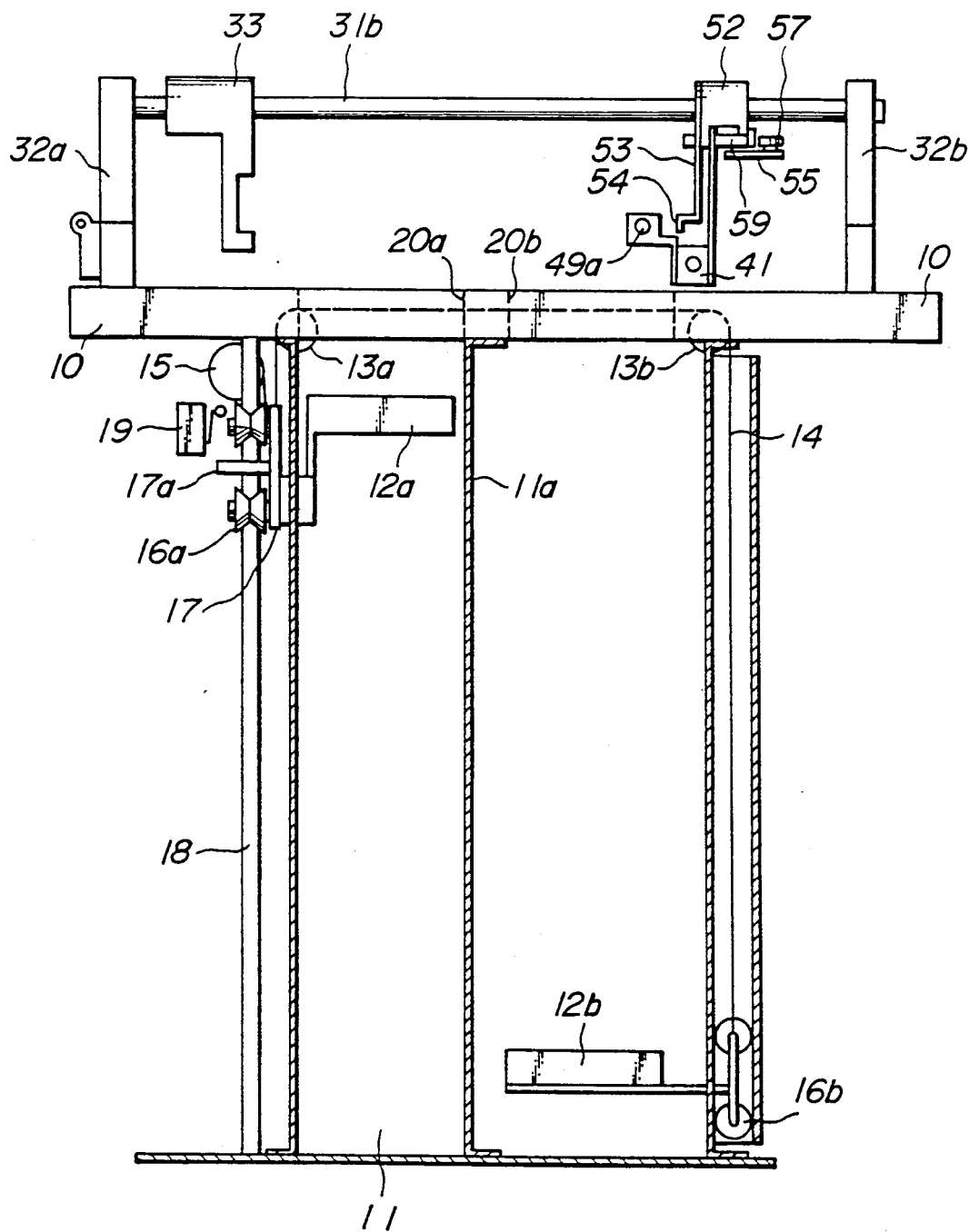
FIG. 3 is a front view illustrating the embodiment shown in FIG. 2.
Figure 4:
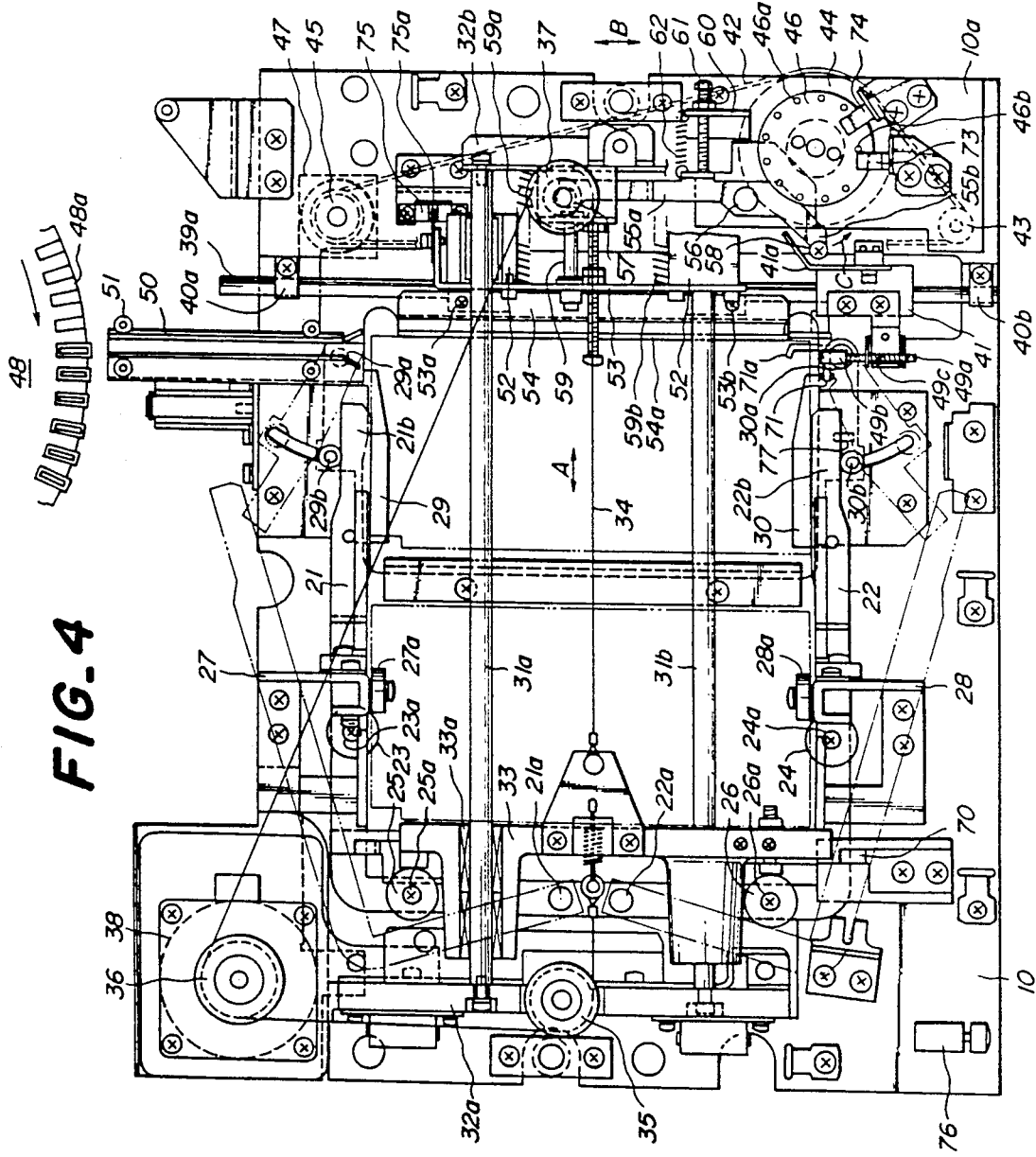
FIG. 4 is a detailed plan view representing the embodiment shown in FIG. 2.
Figure 5:
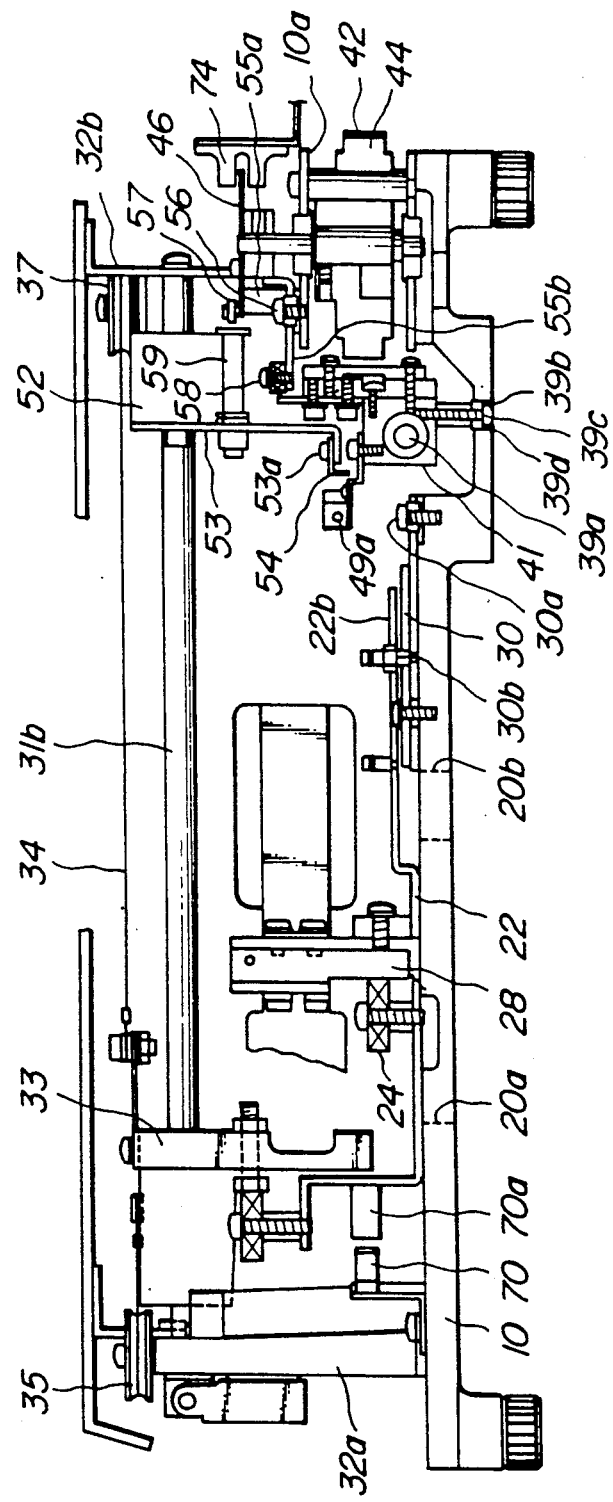
FIG. 5 is a front view showing the cuvette loading portion of the embodiment shown in FIG. 3 in detail.

FIGS. 2 and 4 are schematic plan views and FIGS. 3 and 5 are schematic front views showing an embodiment of the automatic cuvette loader according to the invention. In FIGS. 4 and 5, there is illustrated the detailed construction of the cuvette loading portion of the apparatus.

The cuvette loader comprises a base plate 10 the lower surface of which is secured to a magazine container 11 as best shown in FIG. 3. In the base plate 10 is formed a first opening 20a above the left side space of the magazine container 11 in FIG. 3. The opening 20a having such dimensions that the magazine 1 can pass therethrough. The magazine container 11 is partitioned into two spaces by a wall 11a and magazine supports 12a and 12b are arranged movably up and down in conjunction with each other in these two spaces respectively. A wire 14 is stretched over the magazine container 11 via rollers 13a and 13b, one end of which wire is secured to a connecting member 17 for connecting the magazine support 12a to shafts of a guide bearing 16a and the other end of which is connected to a shaft of a guide bearing 16b which is connected to the magazine support 12b, so that the magazine supports 12a and 12b are moved up and down in opposite directions to each other. The magazine support 12a is moved upward in a stepwise manner along a guide 18 by means of a coiled spring 15 generating a constant force via the connecting member 17 and the guide bearing 16a. The magazines piled up on the magazine support 12a are lifted up above the base plate 10 one by one through the first opening 20a and after the cuvette loading, they are fallen through the second opening 20b and lifted down by the magazine support 12b which is moved downward in conjunction with the upward movement of the magazine support 12a. A limit switch 19 is arranged at an upper position of the container 11 so that the magazine support 12a is not moved upward beyond a predetermined height.

On the upper surface of the base plate 10 are arranged L-shaped levers 21 and 22 rotatably about shafts 21a and 22a, respectively. To these levers are secured ring-shaped stoppers 23 and 24 by means of screws 23a and 24a, respectively. As will be explained later, to the levers 21 and 22 are also secured rollers 25 and 26 by means of screws 25a and 26a. In free ends of the L-shaped levers 21 and 22 are further formed projections 21b and 22b, respectively. Adjacent to the opening 20a of the base plate 10, there are further arranged L-shaped posts 27 and 28 and stoppers 27a and 28a are secured thereto.

In the base plate 10 there is formed the second opening 20b through which the magazine can be passed. Besides the second opening 20b a pair of magazine support levers 29, and 30 are arranged rotatably about shafts 29a and 30a. Near free ends of these levers are secured pins 29b and 30b, respectively. These pins are engaged with the projections 21b and 22b of the L-shaped levers 21 and 22, respectively. The levers 21, 22, 29 and 30 are arranged to be biased into positions shown by dash and dotted lines in FIG. 4 by means of springs not shown.

To the base plate 10 are further secured two guide shafts 31a and 31b by means of leg portions 32a and 32b, and the guide shafts 31a and 31b are extended above the first and second openings 20a and 20b. A first slider 33 is movably secured to the guide shafts 31a and 31b by means of linear bearings 33a. To the first slider 33 is secured a wire 34 which is wound around a pulley 35 provided on the leg portion 32a, a pulley 36 secured to a driving shaft of a motor 38 and a pulley 37 provided on the leg portion 32b. Since the motor 38 is driven in both directions, it is possible to move the first slider 33 in a direction A along the guide shafts 31a and 31b in a reciprocal manner. By this movement, it is possible to transfer the magazine 1 situated above the first opening 20a into a cuvette supplying position which is just situated above the second opening 20b and to feed the cuvettes rows in the magazine one by one in the direction A. For this purpose, to the lower surface of slider 33 are secured four arms 33b which can be inserted in the recesses 1g formed in the magazine 1 and is brought into contact with the push plate 3.

There is further provided a guide shaft 39a extending perpendicularly to the guide shafts 31a and 31b. The guide shaft 39a is coupled with the base plate 10 by means of leg portions 40a and 40b. To this guide shaft 39a is slidably mounted a second slider 41. In the base plate 10, a guide sleeve 39b is extended in parallel with the guide shaft 39a and the second slider 41 is connected to the guide sleeve 39b by means of a shaft 39c which is arranged slidably in the sleeve 39b. To the second slider 41 is connected a wire 42 extending around a pulley 43 arranged near the leg portion 40b, a pulley 44 connected to a shaft of a rotary encoder 46 provided on a plate 10a and a pulley 45 secured to a driving shaft of a motor 47. When the motor 47 is driven in both directions, the second slider 41 can be moved reciprocally in the direction B along the guide shaft 39a and the guide sleeve 39b. By this movement, the cuvettes 2 in the magazine 1 can be inserted into recesses 48a of a cuvette holder 48 provided in an automatic chemical analyzer one by one. To this end, to the second slider 41 is secured a pin 49a. To the head of the pin 49a is provided a pushing claw 49b and around the pin 49a is arranged a coiled spring 49c. Then it is possible to push resiliently the cuvettes 2 situated in an extreme right side row in the magazine 1 in FIG. 4 by means of the pushing claw 49b.

To the guide shafts 31a and 31b is further arranged slidably a third slider 52 by means of linear bearings to which two L-shaped plates 53 and 54 are secured by means of screws 53a and 53b, respectively.

To the plate 46a there is arranged a lever 55 composed of two arms 55a and 55b rotatably about a shaft 56. At tips of the arms 55a and 55b are provided rollers 57 and 58, respectively. To the center portion of the L-shaped plate 53 is also secured a pin 59 which extends in the right hand direction in FIG. 4. At a tip of the pin 59 is secured a small plate which is to be engaged with the roller 57 as will be explained later. To the second slider 41 is secured a cam plate 41a which is selectively engaged with the roller 58 provided at the tip of the arm 55b. Between the leg portion 32b and L-shaped plate 53, there are provided coiled springs 59a and 59b such that the plate 53 is biased to move toward the leg portion 32b. To the plate 10a is also secured an angle member 60 and a screw 61 is provided in the angle member. There is also arranged a coil spring 62 between an upright lug of the arm 55a and the angle member 60 such that the lever 55 is biased to rotate in the clockwise direction in FIG. 4. This rotational movement of the lever 55 is limited by the engagement of the screw 61 and the upright leg of the arm 55a.

At a position corresponding to the outlet 1b of the cuvette magazine 1 situating above the second opening 20b, there is arranged slidably in the direction B a cuvette guide 50 by means of four rollers 51. The cuvettes pushed out from the outlet 1b travel through the cuvette guide 50 to be mounted in recesses 48a provided in the cuvette holder 48 of the automatic chemical analyzer.

Now, the operation of the automatic cuvette loader of this embodiment will be explained.

(1) Set and Transfer Cuvette Magazine

It is assumed that in the magazine container 11 there are set several magazines 1 on the magazine support 12a each containing a hundred cuvettes 2 in a matrix manner. The uppermost magazine is engaged with the stoppers 23 and 24 secured to the L-shaped levers 21 and 22, respectively, so that the magazine stack does not move upwardly any further. After the cuvette loading is finished in the magazine just positioned above the second opening 20b, the first slider 33 is moved toward the starting position (left side position in FIG. 4). The rollers 25 and 26 arranged to the L-shaped levers 21 and 22 are pushed by the first slider at the end of this movement and then the L-shaped levers 21 and 22 are moved outside so as to be situated at the position indicated by dash and dot lines in FIG. 4. In response to the movement of the L-shaped levers 21 and 22, the ring stoppers 23 and 24 are also moved outside. Thus, the uppermost cuvette magazine is lifted upwardly by means of the coiled spring 15 until its upper wall is urged against the ring stoppers 27a and 28a secured to the L-shaped post 27 and 28.

Next the first slider 33 moves to the right side in the direction A along the guide shafts 31a and 31b to transfer the magazine 1 at the cuvette supplying position above the second opening 20b. In accordance with this movement of the first slider 33, the L-shaped levers 21 and 22 and the levers 29 and 30 are returned to the original position, so that the magazine is supported by the levers 29 and 30. When the transferred magazine 1 pushes a cuvette lever 71a which is secured to the base plate 10 rotatably about a shaft 71b, the cuvette lever 71a is rotated and its rotational movement is detected by a lateral slide stop switch 71 and movement of the first slider 33 is stopped.

(2) The movement of the cuvette support

When the first slider 33 starts to move in the right side direction in FIG. 4, the second slider 41 is moved to the lower direction. The cam plate 41a secured to the second slider 41 is also moved in the lower direction and is engaged with the roller 58 secured to the arm 55b of the cuvette support driving lever 55. Then the arm 55b is rotated in the direction shown by an arrow C in FIG. 4. In response to the movement of the arm 55b, the arm 55a pushes the pin 59 secured to the cuvette support 52 via the roller 57 against the force of the springs 59a, 59b. Thus the third slider 52 is slid to the left side in the direction A and is stopped at such a timing that a blade 75a secured to a shoulder of the third slider cuts off a cuvette support stop switch 75. When the switch 75 is cut off, the third slider 52 is situated at a position in which the front plate 54a secured to the third slider 52 is situated just above the front inner side wall of the magazine or slightly inside therefrom. Thereafter, the first slider 33 is further biased to the right side direction, so that the four arms 33b secured to the first slider 33 pushes the plate 3 arranged in the magazine and thus the side walls of the cuvettes situated in the extreme right are urged against the front plate 54a of the cuvette support 52. And the cuvettes moved by the first slider 33 push the lever 71a and the lateral slide stop switch 71 is turned ON. In response to this, the second slider 41 is moved in the upward direction in FIG. 4 up to such a position that a longitudinal slide home position switch 72 is turned OFF. During this movement, the cam plate 41a is separated from the roller 58 on the arm 55b of the cuvette support driving lever 55, and the lever 55 is rotated in the clockwise direction in FIG. 4 by means of the coiled spring 62. And thus, the cuvette support 52 is returned to the original position by means of the coiled springs 59a and 59b.

(3) Cuvette loading

The cuvettes 2 in the magazine 1 are loaded and mounted into the recesses 48a provided in the turntable of the automatic chemical analyzer one by one with the aid of the second slider 41. The second slider 41 is driven by the pulse motor 47 via the timing belt 42. In a rotating disc of the encoder 46 arranged coaxially with the pulley 44 are provided ten holes 46a for detecting the sliding amount of the second slider 41 and one hole 46b for detecting the timing at which the second slider 41 is returned back to the original position. The cuvettes 2 are loaded by the cuvette pushing claw 49b arranged to the second slider 41 one by one. The sliding amount of the second slider 41 for loading one cuvette is detected by a longitudinal slide switch 73 for detecting the holes 46a. For instance, it is designed that when twenty pulses have been supplied to the pulse motor 47, one cuvette is supplied into a recess 48a of the cuvette holder 48.

A longitudinal slide stop switch 74 detects the fact that ten cuvettes in a row have been successively supplied into recesses 48a, and then the pulse motor 47 is driven in the reversed direction so that the second slider 41 is returned back toward the original position until the longitudinal slide home position switch 72 is made ON by the movement of the second slider 41. The cuvette support 52 is slid to the left hand direction in FIG. 4 again in response to the movement of the second slider 41 via the engagement of the cam plate 41a with the roller 58 provided on the lever 55. When the blade 75a secured to the cuvette support 52 cuts off the cuvette support stop switch 75, the second slider 41 is stopped to move. Thereafter, the motor 38 is driven in the forward direction and the first slider 33 is slid to the right hand direction in FIG. 4 to push the plate 3 in the magazine until the side wall of the second cuvette row is urged against the front surface 54a of the L-shaped plate 54. At the same time of the movement of the first slider 33, the pulse motor 47 is driven in the forward direction until the second slider 41 is positioned at the longitudinal slide home position switch 72. By repeating the above mentioned operation all cuvettes 2 in the magazine 1 are loaded and mounted into the recesses 48a of the cuvette holder 48. After the last cuvette 2 is loaded into the cuvette holder 48, the second slider 41 is returned back to turn the switch 72 ON and then is stopped.

(4) Magazine change

The magazine 1 is changed by the manner in the following. After all the cuvettes 2 in the tenth row of the magazine 1 have been loaded, the first slider 33 turns the lateral slide stop switch 77 ON. And then, the motor 38 is reversely driven to move the first slider 33 toward the original position until the first slider 33 turns a lateral slide home position switch 70 ON by means of a blade 70a secured to the shoulder portion thereof and is stopped thereby. And then, the first slider 33 pushes rollers 25 and 26 provided to the L-shaped levers 21 and 22, so that the levers are opened. Therefore, the ends of arms of the lever 21 and 22 push the pins 29b and 30b and then the empty magazine is fallen down through the second opening 10b. A shock absorber is provided on the second magazine support 12b. A new magazine is lifted up through the first opening 20a. When the cuvettes being supplied to the cuvette holder are jammed, a magazine change switch 76 should be turned ON to change the cuvette magazine. When the longitudinal slide start switch 72 is turn ON, the first slider 31 is slid into the original position and a warning signal is signed. Thus, the jammed cuvettes can be aligned or the magazine can be changed by the manual operation of a user.

In case the disposable type cuvettes are used, a cuvette scraping lever 81 is alternatively driven by a motor 82 as best shown in FIG. 2. The cuvette scraping lever 81 is rotatably arranged to scrape the cuvette out of the recess 48a of the cuvette holder 48. In case the cuvettes are washed and used repeatedly, the cuvette scraping lever 81 is remained unoperative.

It may be further provided a cuvette push plate 84 which is driven by a motor 83 by means of a suitable link mechanism. After a cuvette has been inserted into a recess 48a of the cuvette holder 48, the cuvette is pushed down by the cuvette pusher 84, so that the cuvette is mounted in the recess 48a at a precisely determined position. The cuvette guide 50 is arranged to be slidable by means of the rollers 51 in order to make the cuvette supply certainly, and the cuvette guide 50 is slid in the cuvette supply direction in conjunction with the cuvette pusher 84.

The present invention is not limited to the embodiment explained above, but may be modified in various manner. For instance, in the above embodiment one hundred cuvettes are contained in a single magazine, but any desired number of cuvettes may be contained in the magazine.

According to the invention, the reaction cuvettes can be supplied successively into the reaction line smoothly because the outer side walls of the cuvettes situated in the cuvette supply line are not strongly urged against the inner side wall of the cuvette magazine. That is to say, the force of urging by the cuvette magazine against the inner wall of magazine is reduced in comparison with that generated in the conventional automatic cuvette loading machine.

What is claimed is:

1. An automatic cuvette loading apparatus for use in an automatic chemical analyzer having a reaction line comprising:
   a container containing a plurality of magazines, each magazine containing a plurality of cuvettes in a matrix manner and plate means for feeding cuvette rows in a first direction, said container having a base plate and first and second openings through which each magazine can pass;
   means for feeding a magazine situated above said first opening in said first direction into a cuvette loading position above said second opening;
   means for supporting cuvettes situated at said cuvette loading position in said magazine, said cuvette supporting means having a front plate movable in a second direction, substantially opposite to said first direction, to a first position at which said front plate is aligned with or spaced inside of a front inner side wall of said magazine and movable in said first direction to a second position at which said front plate is spaced outside of said front inner side wall of said magazine;
   means movably arranged in a second direction perpendicular to said first direction for successively loading cuvettes situated at said cuvette loading position in said magazine into the reaction line of the chemical analyzer; and
   means for removing an empty magazine from the cuvette loading position through said second opening;
   wherein said cuvette supporting means is arranged in said first position when cuvette rows are urged toward said cuvette loading position by said plate, and is arranged in said second position when cuvettes are loaded into the reaction line by said cuvette loading means.

2. An apparatus according to claim 1, wherein said magazine container comprises a first container comprising a first magazine support for holding a stack of magazines and a second container comprising a second magazine support for holding empty magazines, and means for moving the first and second magazine supports up and down in directions opposite to each other.

3. An apparatus according to claim 2, wherein said magazine feeding means comprises a first slider movably arranged in said first direction between a position above said first opening of said container and said cuvette loading position, and means for reciprocating said first slider in said first direction.

4. An apparatus according to claim 3, wherein said cuvette loading means comprises a second slider the second slider constructed so as to push a cuvette row aligned in said magazine in a second direction, and means for reciprocating the second slider in said second direction.

5. An apparatus according to claim 4, wherein said cuvette supporting means comprises a third slider movably arranged between said first position and said second position, and means for mechanically transmitting movement of said cuvette loading means to said third slider.

6. An apparatus according to claim 5, wherein said magazine removing means comprises means for allowing an empty magazine to fall through said second opening due to gravitational force.

7. An apparatus according to claim 2, wherein said magazine container further comprises stopper means for inhibiting the upward movement of said magazine stack, the inhibiting effect of said stopper means being disengaged by means of said first slider of said magazine feeding means.

8. An apparatus according to claim 7, wherein said empty magazine removing means is made operative in conjunction with movement of said stopper means.

9. An apparatus according to claim 3, wherein said first slider is constructed so as to arrange cuvettes in said magazine in said cuvette loading position.

10. An apparatus according to claim 5, wherein said cuvette supporting means further comprises stopper means for inhibiting movement of said third slider beyond said first position, and means for returning said third slider to said second position while cuvettes are supplied to said reaction line of said chemical analyzer.

11. An apparatus according to claim 1, wherein said apparatus further comprises means for pushing down a cuvette mounted in a cuvette receiving part of said chemical analyzer to stabley mount said cuvette therein.

12. An apparatus according to claim 1, further comprising means for removing cuvettes from a cuvette receiving part of said chemical analyzer.

13. An automatic cuvette loading apparatus for use in an automatic chemical analyzer having a reaction line comprising:

means for receiving a plurality of magazines arranged one on the other, each of said magazines comprising a rectangular housing having a top, bottom, and side walls, an outlet provided in a first side wall for discharging cuvettes one by one, and a height of a second side wall adjacent to said first side wall being smaller than that of the remaining side walls so as to form a window;

means for successively feeding magazines contained in said magazine receiving means in a first direction into a cuvette loading position;

means for moving cuvettes in one cuvette row contained in said magazine situated at said cuvette loading position in a second direction perpendicular to said first direction one by one through said outlet of said magazine into said reaction line;

means for pushing a plate arranged within said magazine into said first direction to move cuvette rows in said magazine after loading of one cuvette row has been completed, thereby moving a new row of cuvettes into said cuvette loading position;

means including a cuvette support member arranged movably in said first direction between a first position in which said cuvette support member is engaged with cuvettes in a row situated at said cuvette loading position through said window formed in said second side wall of said magazine, and a second position at which said cuvette support member is separated from said magazine; and means for moving said cuvette support member between said first and second positions such that when a cuvette row within said magazine is moved by means of said plate, said cuvette support member is in said first position and when cuvettes in a row situated at said cuvette loading position are fed, said cuvette support member is in said second position.

14. An apparatus according to claim 13, wherein said cuvette support member is constructed so as to move between said first and second positions when said means for moving the cuvettes in the cuvette row situated at said cuvette loading position is moved.

15. An apparatus according to claim 1, further comprising drive means for moving said front plate to said first position when cuvette rows are fed toward said cuvette loading position by means of said plate, and to said second position when cuvettes in a cuvette row situated at said cuvette loading position are loaded into said reaction line by said cuvette loading means.

* * * * *